United States Patent
Ahmad et al.

(10) Patent No.: US 9,919,124 B2
(45) Date of Patent: *Mar. 20, 2018

(54) DELIVERY ADAPTOR FOR VENTILATION SYSTEM

(71) Applicant: Breathe Technologies, Inc., Irvine, CA (US)

(72) Inventors: Samir S. Ahmad, San Diego, CA (US); Mark J. Zechmeister, Costa Mesa, CA (US); Enrico Brambilla, Irvine, CA (US); Leonardo Alberto Baloa Welzien, Lake Forest, CA (US)

(73) Assignee: Breathe Technologies, Inc., Irvine, CA (US)

( * ) Notice: Subject to any disclaimer, the term of this patent is extended or adjusted under 35 U.S.C. 154(b) by 570 days.

This patent is subject to a terminal disclaimer.

(21) Appl. No.: 13/927,008

(22) Filed: Jun. 25, 2013

(65) Prior Publication Data

US 2014/0373835 A1 Dec. 25, 2014

(51) Int. Cl.
*A61M 16/00* (2006.01)
*A62B 7/00* (2006.01)
*A61M 16/08* (2006.01)
*A61M 16/16* (2006.01)
*A61M 16/20* (2006.01)

(52) U.S. Cl.
CPC .... *A61M 16/0875* (2013.01); *A61M 16/0833* (2014.02); *A61M 16/0858* (2014.02); *A61M 16/16* (2013.01); *A61M 16/0066* (2013.01); *A61M 16/20* (2013.01); *A61M 2016/0027* (2013.01); *A61M 2202/0208* (2013.01)

(58) Field of Classification Search
CPC ...... A61M 2210/0618; A61M 16/0666; A61M 16/0816; A61M 16/0875; A61M 16/00; A61M 25/00
USPC ............. 128/207.13, 201.13, 205.24, 207.18
See application file for complete search history.

(56) References Cited

U.S. PATENT DOCUMENTS 5,681,063 A * 10/1997 Bressner ............ A61M 39/1011
285/123.1
7,762,253 B2 * 7/2010 Acker ............... A61M 16/0666
128/202.27

* cited by examiner

*Primary Examiner* — Kari Rodriquez
*Assistant Examiner* — Victoria Murphy
(74) *Attorney, Agent, or Firm* — Stetina Brunda Garred and Brucker; Mark B Garred (57) ABSTRACT

In accordance with the present invention, there is provided is provided a tubing arrangement and associated connectors, including a delivery adaptor and a Y-connector, which may be used to facilitate the operative interface of a patient interface to a ventilator within a ventilation system. The delivery adaptor is connected between the outlet connector of the flow generator and the main delivery tube (i.e., the quad-lumen tube) in the ventilation system. The delivery adaptor functions to retain the pneumatic isolation of a sense line of the ventilation system from certain other lumens of the quad-lumen tube, and further connects one of the small lumens of the quad-lumen tube to an external oxygen source or an external humidification source. The oxygen or humidification is delivered to such lumen through the adaptor. The oxygen or humidification is then bled into the air stream at the outlet of such lumen which is at the Y-connector.

19 Claims, 6 Drawing Sheets

DELIVERY ADAPTOR FOR VENTILATION SYSTEM

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to an adapter or attachment for a ventilation system such as an obstructive sleep apnea (OSA) system that allows for the delivery of humidification or low pressure oxygen to the patient.

2. Description of the Related Art

As is known in the medical arts, mechanical ventilators comprise medical devices that either perform or supplement breathing for patients. The vast majority of contemporary ventilators use positive pressure to deliver gas to the patient's lungs via a patient circuit between the ventilator and the patient. The patient circuit typically consists of one or two large bore tubes (e.g., from 22 mm ID for adults to 8 mm ID for neonatal) that interface to the ventilator on one end, and a patient mask on the other end. Most often, the patient mask is not provided as part of the ventilator system, and a wide variety of patient masks can be used with any ventilator.

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

Vented patient circuits are used only to carry gas flow from the ventilator to the patient and patient mask, and require a patient mask with vent openings. When utilizing vented circuits, the patient inspires fresh gas from the patient circuit, and expires CO2-enriched gas, which is purged from the system through the vent openings in the mask. When utilizing non-vented dual limb circuits, the patient inspires fresh gas from one limb (the "inspiratory limb") of the patient circuit and expires CO2-enriched gas from the second limb (the "expiratory limb") of the patient circuit. Both limbs of the dual limb patient circuit are connected together in a "Y" proximal to the patient to allow a single connection to the patient mask. When utilizing non-vented single limb circuits, an expiratory valve is placed along the circuit, usually proximal to the patient. During the inhalation phase, the exhalation valve is closed to the ambient and the patient inspires fresh gas from the single limb of the patient circuit. During the exhalation phase, the patient expires CO2-enriched gas from the exhalation valve that is open to ambient.

In the patient circuits described above, the ventilator pressurizes the gas to be delivered to the patient inside the ventilator to the intended patient pressure, and then delivers that pressure to the patient through the patient circuit. Very small pressure drops develop through the patient circuit, typically around 1 cmH2O, due to gas flow though the small amount of resistance created by the tubing. Some ventilators compensate for this small pressure drop either by mathematical algorithms, or by sensing the tubing pressure more proximal to the patient.

In patients with obstructive sleep apnea (OSA), the clinical evidence for continuous positive airway pressure (CPAP) and bi-level PAP as therapy for improving the quality of life is mounting. Over the past few decades, CPAP therapy for obstructive sleep apnea has evolved into more and more sophisticated modes of therapy for various forms of sleep-disordered breathing. CPAP, as the name implies, requires the airway pressure to be constant between inspiration and expiration. In many applications, such a pressure is achieved through the use of an air compressor which is controlled in a manner as maintains the airway pressure as closely to the prescribed pressure despite the pull (inspiration) and push (exhalation) of the patient. Bi-level PAP therapy was originally conceived with the idea of varying the administered pressure between the inspiratory and expiratory cycles. In concept, such a variable pressure setting decreases the amount of pressure against which the patient exhales, thereby decreasing abdominal muscle recruitment and consequent respiratory discomfort during the expiratory cycle. Moreover, during the inspiratory cycle, the greater level of pressure assist would combat the inspiratory flow limitation suffered by the upper airway.

For patients on CPAP or bi-level therapy for OSA, there is often a need to have supplemental low pressure, low flow oxygen. A number of solutions are currently known to provide such oxygen. In one currently known, commonly used solution, the oxygen is bled directly into the mask through connection ports normally supplied in the frame of the mask itself. In another currently known, commonly used solution, the oxygen is bled using an adapter connected between the flow generator device and the usual 22 mm delivery tube.

However, these known solution present certain disadvantages which detract from their overall utility. More particularly, with regard to the former solution, the same has the disadvantage of offering poor oxygen mixing and the continuous delivery of oxygen directly into the mask even when the flow generator device is not working (e.g. stops working because of a fault or is turned off by the patient). Another disadvantage is the presence of an additional oxygen tube that connects to the mask. With regard to the latter solution, though the same has the advantage of offering a convenient location for the oxygen connection, it suffers from the disadvantage of exposing the flow generator to potentially high oxygen concentrations in the case of a high patient tidal volume that results in back flow into the device during exhalation. Normally, standard CPAP or bi-level devices are not designed to operate in an oxygen rich environment which could otherwise lead to a member of problems. The present invention addresses the deficiencies of the prior art by providing an oxygen delivery solution similar to the latter solution described above, but eliminating its aforementioned shortcomings.

For patients on CPAP or bi-level therapy for OSA, there is also often a need to have supplemental humidification provided to the patient. In normal, unassisted respiration, heat and moisture are absorbed from the exhaled air by the inner walls of the oral and nasal cavities of the patient as the air travels from the patient's lungs to the outside environment. This heat and moisture is then transferred to the inhaled air in the next breath, helping to keep the mucus membranes of the patient's lungs humidified and at the proper temperature. Mechanical ventilation bypasses this natural system, often resulting in dry air of incorrect temperature being introduced into the oral and nasal cavities, and hence the lungs of the patient. After a period of time, the respiratory tract of the ventilated patient becomes dried, often causing discomfort. Thus, one of the known disadvantages of conventional breathing circuits is that the air delivered to the patient's lungs is not at the appropriate humidity and/or temperature level.

In order to provide for proper humidity and temperature of the air in ventilator and breathing circuits, it is known to integrate a heat and moisture exchange (HME) device into the breathing circuit. Typically, HME devices are placed into the breathing circuit somewhere within the flow path of the warm, moist air which is exhaled by the patient. The exhaled air enters the HME device, where the moisture and heat are absorbed by those materials used to fabricate the same. These materials then impart the absorbed heat and moisture to the inhaled air in the next breath. The retention of warmth and high humidity helps to prevent the patient's lungs and mucus layers from drying out. Currently known HME devices generally consist of a housing that contains a layer of flexible, fibrous, gas-permeable media or material. As indicated above, this media has the capacity to retain moisture and heat from the air that is exhaled from the patient's lungs, and then transfer the captured moisture and heat to the inhaled air when the patient is inhaling with the assistance of the flow generator. The fibrous material or media in the HME device may be made of foam or paper or other suitable materials that are untreated or treated with hygroscopic material. However, in certain circumstances, the level of humidification imparted by the HME is insufficient for proper patient comfort, thus necessitating that it be supplemented with or replaced by a more robust form of humidification emanating from a humidifier integrated into the breathing circuit. The present invention also addresses the aforementioned humidification deficiencies of prior art HME devices by providing a humidification delivery solution.

BRIEF SUMMARY OF THE INVENTION

In accordance with the present invention, there is provided a tubing arrangement and associated connectors, including a delivery adaptor and a Y-connector, which may be used to facilitate the operative interface of a patient interface to a ventilator within a ventilation system, such as an OSA ventilation system. A preferred patient interface is a mask, such as a nasal pillows mask, which is outfitted with a piloted exhalation valve. The tubing arrangement may comprise a pair of bi-lumen tubes. One end of each of the bi-lumen tubes is fluidly connected to the mask, with the opposite end being fluidly connected to the Y-connector. The Y-connector is in turn fluidly connected to one end of a main delivery tube also included in the tubing arrangement, such main delivery tube preferably being a quad-lumen tube. The opposite end of the quad-lumen tube is fluidly connected to the delivery adaptor, which is in turn fluidly coupled to the outlet connector of a flow generator of the ventilation system. The Y-connector is uniquely configured to fluidly connect certain lumens of the quad-lumen tube to dedicated, corresponding ones of the lumens included in respective ones of the bi-lumen tubes, and to further allow for the selective detachment of the quad-lumen tube from the bi-lumen tubes.

As indicated above, the delivery adaptor is connected between the outlet connector of the flow generator and the main delivery tube (i.e., the quad-lumen tube) in the ventilation system. The main lumen of the quad-lumen tube is used for delivering a breathable gas (normally air) to the patient via a patient interface or mask. One of the small lumens of the quad-lumen tube is used for mask/patient pressure sensing, with one other small lumen being used to pilot the exhalation valve integrated into the mask. The delivery adaptor functions to retain the pneumatic isolation of the sense line of the ventilation system from the other lumens.

In one embodiment of the present invention, the last (i.e., third) small lumen of the quad-lumen tube, which is normally not used, may be pneumatically short-circuited with the main lumen at the Y-connection with the mask facilitated by the Y-connector. In this instance, the delivery adaptor connects the third, normally not used small lumen of the quad-lumen tube to an external oxygen source. The oxygen is delivered to the third lumen through the adaptor. The oxygen is then bled into the air stream at the outlet of the third lumen which is at the Y-connector. Oxygen is thus bled away from the flow generator but before the mask, in a high turbulence area that will allow excellent mixing. As a result, the chances of having oxygen back flow in the flow generator are remote even during a flow generator fault, since the path of least resistance is through the mask/valve. Along these lines, in the ventilation system including the adaptor, there is always a positive gas flow from the flow generator to the patient due to the presence of the exhalation valve in the mask.

In another embodiment of the present invention, the delivery adaptor connects the third, normally not used small lumen of the quad-lumen tube to an external humidification source (e.g., a humidifier including a water supply) rather than to an external oxygen source. In this embodiment, water is delivered to the third lumen through the adaptor. The water is then infused into the air stream at the outlet of the third lumen which is at the Y-connector. The modality used to facilitate the connection of the quad-lumen tube to the Y-connector may include a humidity delivery system which interacts with the third lumen, such as a selectively permeable membrane (e.g., Gore-Tex®) that delivers gaseous water, a valve that delivers small droplets of water, or a nebulizer that delivers pulverized water. In each of these solutions, the water is delivered (in different forms) in the aforementioned highly turbulent area of the Y-connector in order to facilitate mixing with the breathable gas. The third lumen or water line is further connected to a pressure source in order to drive the water delivery. The pressure source may be a device integrated into the humidifier or alternatively may be the flow generator or blower of the ventilator integrated into the ventilation system.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

Figure 1:
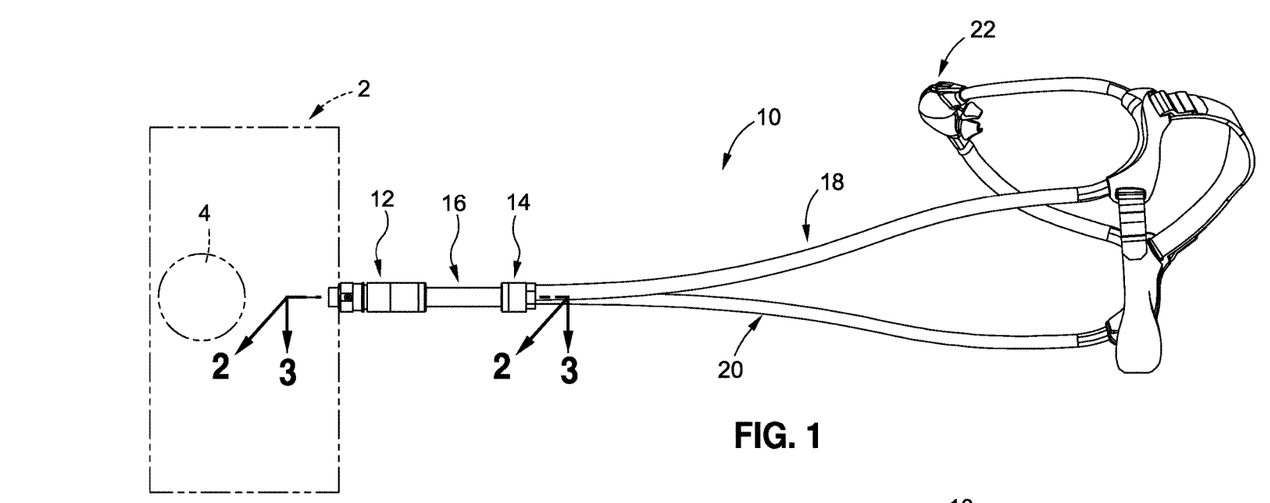
FIG. 1 is a perspective view depicting a tubing arrangement comprising a delivery adaptor, a quad-lumen tube, a Y-connector, and pair of bi-lumen tubes which are constructed in accordance with the present invention and used to collectively facilitate the operative interface between a ventilation mask and a flow generating device or ventilator which is shown in phantom.

Referring now to the drawings wherein the showings are for purposes of illustrating preferred embodiments of the present invention only, and not for purposes of limiting the same, FIG. 1 depicts an exemplary tubing arrangement 10 which may be used to facilitate the operative connection of a patient interface to a ventilator 11 within a ventilation system, such as an OSA ventilation system. The tubing arrangement 10 includes a delivery adapter 12, a Y-connector 14, a main delivery or quad-lumen tube 16 which fluidly couples the delivery adapter 12 and the Y-connector 14 to each other, and an identically configured pair of first and second bi-lumen tubes 18, 20 which fluidly couple the Y-connector 14 to the patient interface. In the exemplary tubing arrangement 10, the preferred patient interface is a mask, and more particularly a nasal pillows mask 22 which is outfitted with a piloted exhalation valve. In this regard, the structural and functional attributes of the mask 22 are described with particularity in Applicant's U.S. patent application Ser. No. 13/784,561 entitled VENTILATION MASK WITH INTEGRATED PILOTED EXHALATION VALVE filed Mar. 4, 2013, the disclosure of which is incorporated herein by reference.

Figure 6:
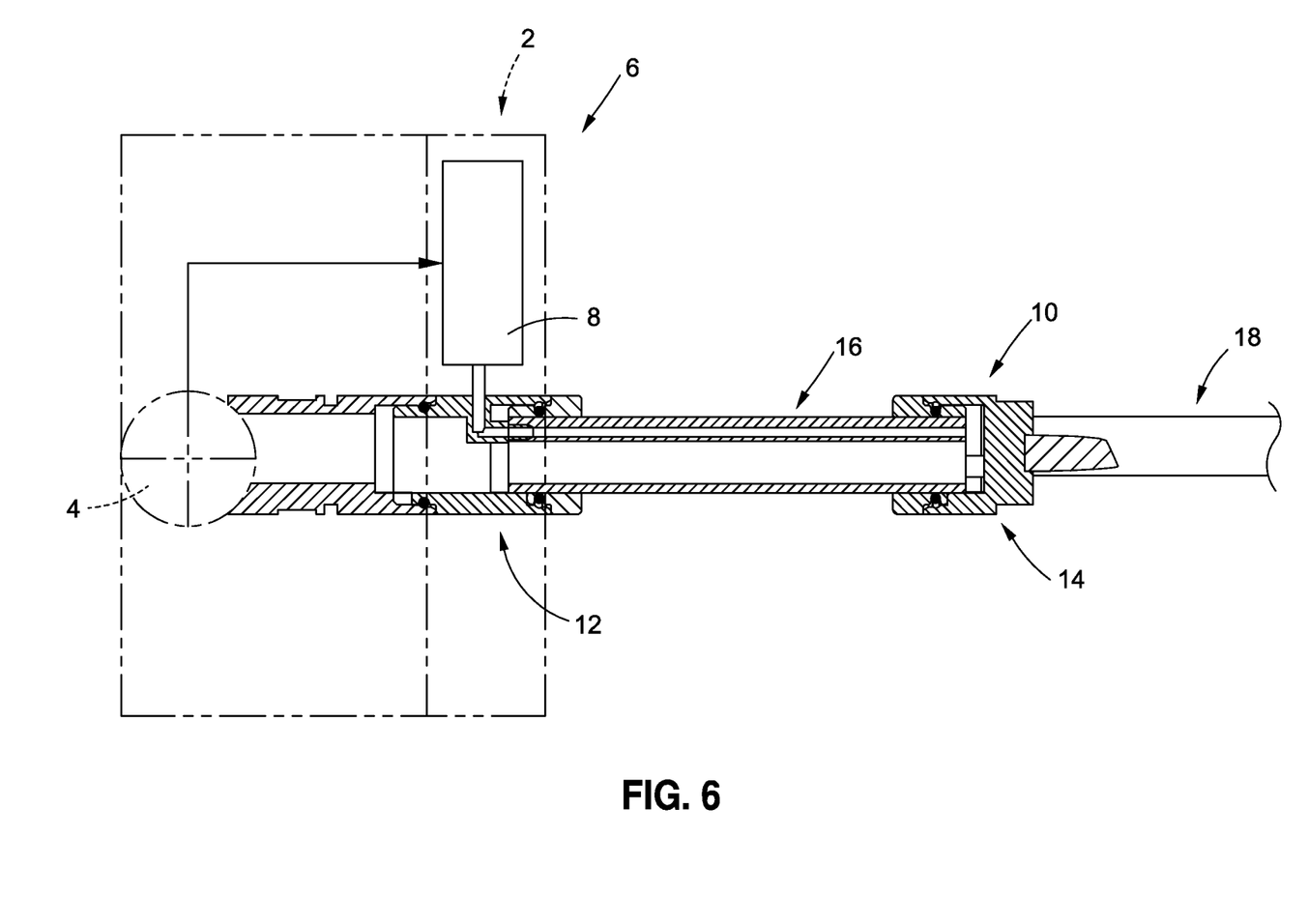
FIG. 6 is a cross-sectional view similar to FIG. 2, but further depicting the operative interface of the tubing arrangement to one embodiment of a humidifier optionally integrated into the ventilator.
Figures 7, 8:
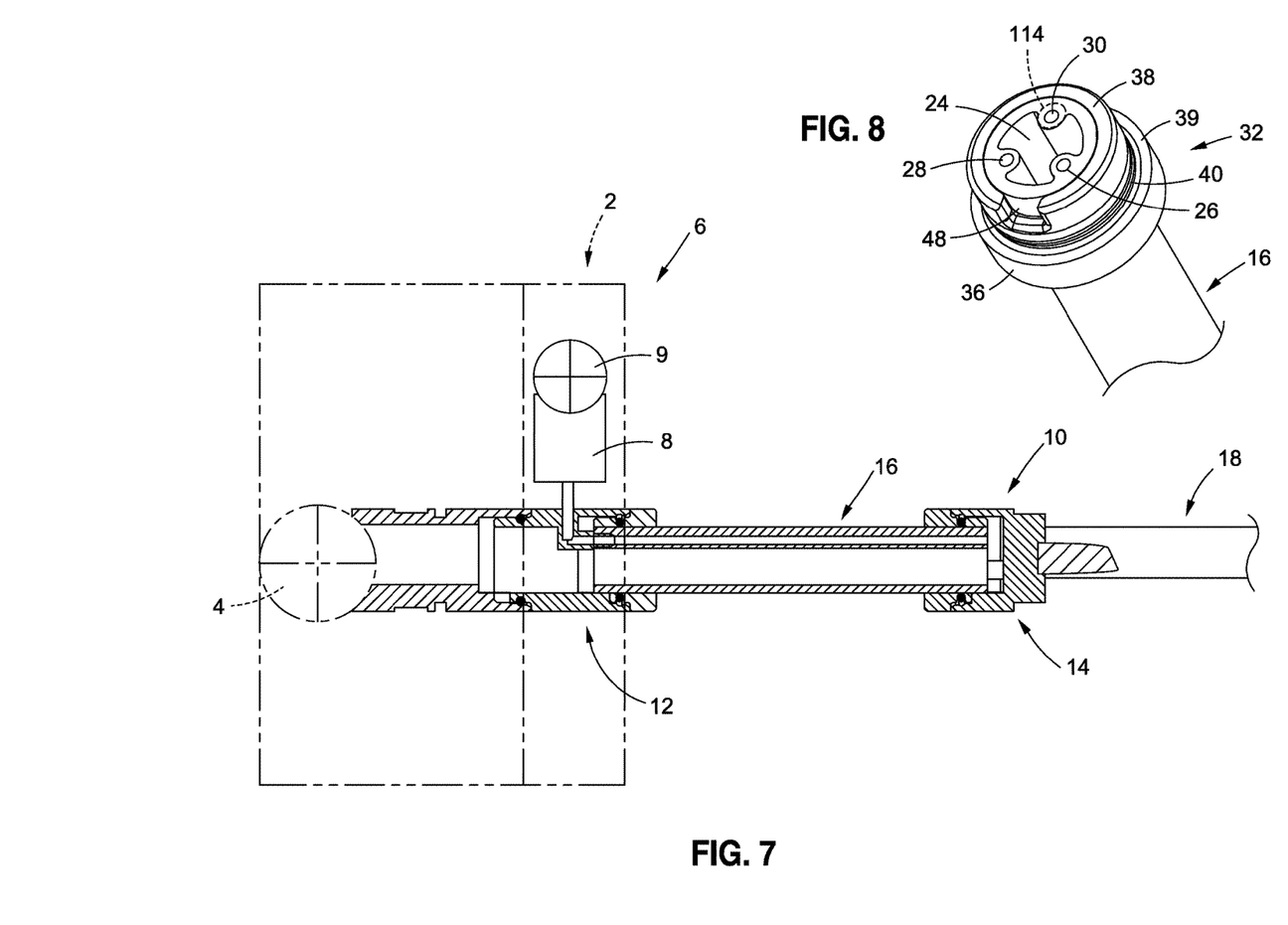
FIG. 7 is a cross-sectional view similar to FIG. 6, but further depicting the operative interface of the tubing arrangement to another embodiment of a humidifier optionally integrated into the ventilator.
FIG. 8 is an enlarged partial perspective of the male member of the Y-connector as interfaced to the quad-lumen tube taken from FIG. 5, but further depicting in phantom a humidity delivery device that may be interfaced to the auxiliary lumen of the quad-lumen tube.

The ventilator 2 is shown in phantom in FIGS. 1, 6 and 7. Typically, the ventilator 2 comprises an exterior housing which accommodates several other components or features. These components include a blower or flow generator 4 which receives a breathable gas from an inlet port of the ventilator 2, and expels pressurized breathable gas from an outlet port thereof. The breathable gas typically comprises air, though it may alternatively comprise other therapeutic gas mixtures. The inlet and outlet ports are at least partially defined by inlet and outlet connectors, respectively, which are typically disposed within a common exterior surface of the ventilator housing. As seen in FIGS. 6 and 7, in accordance with one aspect of the present invention, the ventilator 2 may further optionally include a humidifier 6 which is disposed within the housing thereof. The structural features of the humidifier 6, and its functionality in the context of the present invention, will be described in more detail below.

In the tubing arrangement 10, one end of each of the first and second bi-lumen tubes 18, 20 is fluidly connected to the mask 22, with the opposite end being fluidly connected to the Y-connector 14. In addition, one end of the quad-lumen tube 16 is fluidly connected to the Y-connector 14, with the opposite end being fluidly connected to the delivery adaptor 12, which is in turn adapted to be fluidly connected to the outlet connector of the ventilator 2. The structural and functional attributes of each of the first and second bi-lumen tubes 18, 20, the structural and functional attributes of the Y-connector 14, the structural and functional attributes of the quad-lumen tube 16, and the manner in which the first and second bi-lumen tubes 18, 20 are fluidly connected to both the mask 22 are describe with particularity in Applicant's U.S. patent application Ser. No. 13/798,931 entitled VENTILATION MASK WITH INTEGRATED PILOTED EXHALATION VALVE filed Mar. 13, 2013, the disclosure of which is also incorporated herein by reference. Applicant's U.S. patent application Ser. No. 13/798,931 provides a comprehensive description of not only the structural and functional attributes of the Y-connector 14, but also the manner in which such Y-connector 14 is fluidly coupled to both the quad-lumen tube 16 and the first and second bi-lumen tubes 18, 20 as effectuates the fluid communication between the quad-lumen tube 16 and the mask 22 via the intervening Y-connector 14 and first and second bi-lumen tubes 18, 20.

Though, as indicated above, the preferred mask 22 is the nasal pillows mask described with particularity in Applicant's U.S. patent application Ser. No. 13/784,561, those skilled in the art will recognize that other ventilation masks are contemplated herein, such as nasal prongs masks, nasal masks, full face masks and oronasal masks. As such, for purposes of this application, the term mask and/or ventilation mask is intended to encompass all such mask structures. As also indicated above, the mask 22 preferably includes an integrated, diaphragm-implemented, piloted exhalation valve.

As is described with particularity in Applicant's U.S. patent application Ser. No. 13/798,931, the quad-lumen tube 16 has a generally circular, cross-sectional configuration, and defines four (4) lumens. More particularly, the quad-lumen tube 16 includes a main gas delivery lumen 24, a pressure sensing lumen 26, a pilot lumen 28, and an auxiliary lumen 30. The pressure sensing, pilot and auxiliary lumens 26, 28, 30 are preferably disposed about the gas delivery lumen 24 in equidistantly spaced intervals of approximately 120°, and have identically dimensioned, generally circular cross-sectional configurations.

The gas delivery lumen 24 defined by the quad-lumen tube 16 does not have a generally circular cross-sectional configuration. Rather, portions of the quad-lumen tube 16 which accommodate respective ones of the pressure sensing, pilot and auxiliary lumens 26, 28, 30 protrude into the gas delivery lumen 24, thus imparting a generally cloverleaf cross-sectional configuration thereto. Such cross-sectional profile of the quad-lumen tube 16 is present along the entire length thereof. In the quad-lumen tube 2000, the auxiliary lumen 30 is used to provide oxygen flow, as will be discussed in more detail below.

The quad-lumen tube 16 is preferably fabricated from a silicone, TPE or PVC material which has a Shore Hardness in the range of from about 50 A to about 80 A, and thus possesses a prescribed level of resilience and flexibility. Though not shown, it is contemplated that the quad-lumen tube 16 may have a spiral-shaped reinforcement ribbon embedded therein to enhance the structural integrity thereof, thus making the gas delivery, pressure sensing, pilot and auxiliary lumens 24, 26, 28, 30 less susceptible to collapse upon any excessive bending or compression of the quad-lumen tube 16. It is also contemplated that the ribbon could be substituted with a reinforcement braiding which is adapted to enhance the structural integrity of the quad-lumen tube 16 in the aforementioned manner. However, those or ordinary skill in the art will recognize that the quad-lumen tube 16 need necessarily have the ribbon or other type of reinforcement braiding integrated therein. Along these lines, it is also contemplated that the quad-lumen tube 16 could further be alternatively configured such that the pressure sensing, pilot and auxiliary lumens 26, 28, 30 assume a generally helical profile along the length thereof, thus mimicking the effect of the effect of the ribbon, and assisting in the prevention of the kinking or collapse of the quad-lumen tube 16. In FIGS. 1-5, the quad-lumen tube 16 is depicted in the tubing arrangement 10 in a very short length, solely for purposes of simplicity. In this regard, in a normal application, the length of the quad-lumen tube 16 will typically be about six (6) feet.

Figure 3:
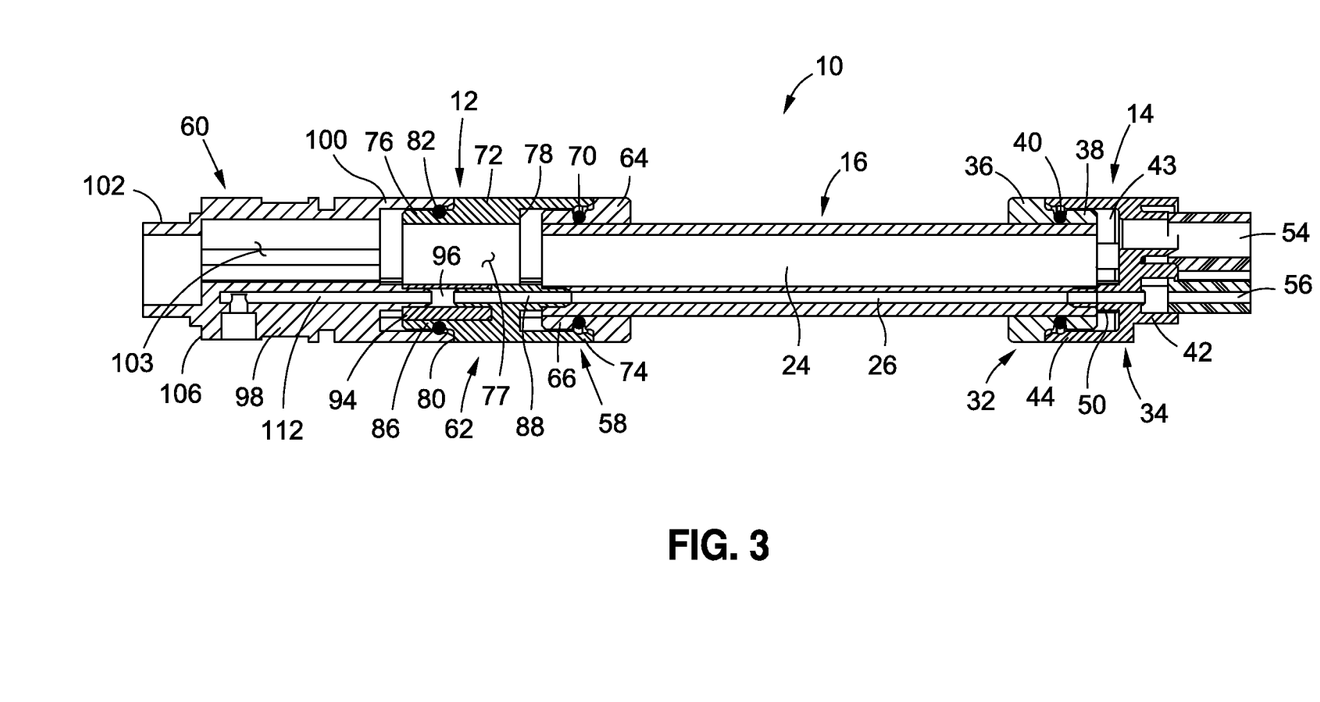
FIG. 3 is a cross-sectional view taken along line 3-3 of FIG. 1.

As also described with particularity in Applicant's U.S. patent application Ser. No. 13/798,931, the first and second bi-lumen tubes 18, 20 are identically configured to each other, and each have a generally tear-drop shaped cross-sectional configuration. The first and second bi-lumen tubes 18, 20 are also each of a prescribed length. The first bi-lumen tube 18 includes a gas delivery lumen 54 and a pressure sensing lumen 56, both of which are shown in FIG. 3. Similarly, the second bi-lumen tube 20 includes a gas delivery lumen which is identically configured to the gas delivery lumen 54, and a pilot lumen which is identically configured to the pressure sensing lumen 56. Each bi-lumen tube 18, 20 is preferably fabricated from a silicone, TPE or PVC material which has a Shore Hardness in the range of from about 50 A to about 80 A, and thus possesses a prescribed level of resilience and flexibility. The structural features of the first and second bi-lumen tubes 18, 20 coupled with the material properties thereof, are selected to not only to provide resilient flexibility, but to prevent either of the pressure sensing lumen 56 or pilot lumen from being collapsed by even an above-normal level of bending, twisting or other deflection of the corresponding bi-lumen tube 18, 20. In this regard, the elliptical or tear drop shaped cross-sectional configuration of each bi-lumen tube 18, 20, coupled with the orientation of the corresponding pressure sensing lumen 56 or pilot lumen, substantially reduces the susceptibility of the pressure sensing lumen 56 or pilot lumen to inadvertent collapse.

In the tubing arrangement 10, the Y-connector 14 is adapted to allow for the selective disconnection or de-coupling of the quad-lumen tube 16 from the first second bi-lumen tubes 18, 20 without disconnecting or separating either the quad-lumen tube 16 or either of the first and second bi-lumen tubes 18, 20 from the Y-connector 14. In this regard, as explained in detail in Applicant's U.S. patent application Ser. No. 13/798,931 referred to above, the Y-connector 14 comprises a male member 32 and a complimentary female member 34 which are releasably engageable to each other. The male member 32 has a generally annular, sleeve-like configuration defining a first portion 36 which is of a first outer diameter and transitions into a second portion 38 which is of a second outer diameter less than the first outer diameter. In this regard, the first and second portions 36, 38 are separated from each other by a continuous, annular shoulder 39. Formed within the outer surface of the second portion 38 is a continuous groove or channel which is disposed in relative close proximity to the shoulder 39 and accommodates a complimentary O-ring 40. The O-ring 40 protrudes slightly outwardly beyond the outer surface of the second portion 38.

The male member 32 of the Y-connector 14 is advanced over and frictionally engaged to that end portion of the quad-lumen tube 16 opposite that which is fluidly connected to the adaptor 12 included in the exemplary tubing arrangement 10. More particularly, the male member 32 is oriented such that a corresponding end of the quad-lumen tube 16 is substantially flush or continuous with the distal end or rim defined by the reduced diameter second portion 38 of the male member 32.

The female member 34 of the Y-connector 14 comprises a base portion 42 which has a generally tear-drop shaped configuration. Integrally connected to the base portion 42 is an annular sleeve portion 44 which has a generally circular cross-sectional configuration. The base and sleeve portions 42, 44 collectively define a hollow cavity 43 of the female member 34. Disposed within the inner wall or surface of the sleeve portion 44 is a continuous groove or channel 45. The channel 45 is sized and configured to accommodate that portion of the O-ring 40 which protrudes from the outer surface of the second portion 38 of the male member 32 when the male and female members 32, 34 are releasably engaged to each. Also formed on the inner wall or surface of the sleeve portion 44 proximate the channel is an alignment tab 46, the size and shape of which is complimentary to that of a slot 48 which is formed within the second portion 38 of the male member 32. In this regard, the slot 48 is sized and configured to accommodate the tab 46 when the male and female members 32, 34 are releasably engaged to each other.

Formed in the base portion 42 of the female member 34 in side-by-side relation to each other is an identically configured pair of first and second openings, each of which has a generally tear-drop shaped profile which is complimentary to the cross-sectional configuration of each of the first and second bi-lumen tubes 18, 20. The female member 34 further includes an identically configured pair of first and second gas delivery ports which are each formed on the base portion 42 within respective ones of the first and second openings therein. The first and second gas delivery ports each have a tubular, generally cylindrical configuration with a generally circular cross-sectional profile. Further, the first gas delivery port defines a first gas delivery lumen, with the second gas delivery port defining a second gas delivery lumen. The first and second gas delivery lumens each fluidly communicate with the cavity 43 of the female member 34.

The female member 34 further comprises a pressure sensing port 50 and a pilot port 52 which are identically configured to each other, and are formed on the base portion 42 so as to protrude into the cavity 45 in spaced, generally parallel relation to each other. The pressure sensing and pilot ports 50, 52 also each have a tubular, generally cylindrical configuration with a generally circular cross-sectional profile. The pressure sensing port 50 defines a pressure sensing lumen, with the pilot port 52 defining a pilot lumen. The pressure sensing lumen fluidly communicates with the first opening proximate the first gas delivery port. Similarly, the pilot lumen fluidly communicates with the second opening proximate the second gas delivery port.

In interfacing the first and second bi-lumen tubes 18, 20 to the female member 34 of the Y-connector 14, one end portion of the first bi-lumen tube 18 is advanced into the complimentary first opening of the female member 34 in a manner wherein the first gas delivery port is concurrently advanced into and frictionally retained within a corresponding end of the gas delivery lumen 54 of the first bi-lumen tube 18 in the manner shown in FIG. 3. The advancement of the first gas delivery port into the gas delivery lumen 54 is limited by the abutment of the end of the first bi-lumen tube 18 against the bottom of the first opening defined by the base portion 42 of the female member 34. Due to the complimentary shapes of the first opening and the first bi-lumen tube 18, the abutment of the end of the first bi-lumen tube 18 against the bottom of the first opening facilitates the general coaxial alignment (and fluid communication) between the pressure sensing lumen (and hence the pressure sensing port 50) of the female member 34 and the pressure sensing lumen 56 of the first bi-lumen tube 18.

In a similar fashion, one end portion of the second bi-lumen tube 20 is advanced into the complimentary second opening in a manner wherein the second gas delivery port of the female member 34 is advanced into and frictionally retained within a corresponding end of the gas delivery lumen of the second bi-lumen tube 20. The advancement of the second gas delivery port into the gas delivery lumen of the second bi-lumen tube 20 is limited by the abutment of the end of the second bi-lumen tube 20 against the bottom of the second opening defined by the base portion 42 of the female member 34. Due to the complimentary shapes of the second opening and the second bi-lumen tube 20, the abutment of the end of the second bi-lumen tube 20 against the bottom of the second opening facilitates the general coaxial alignment (and fluid communication) between the pilot lumen (and hence the pilot port 52) of the female member 34 and the pilot lumen of the second bi-lumen tube 20.

As indicated above, in the ventilation system including the tubing arrangement 10, the Y-connector 14 facilitates the operative interface between the quad-lumen tube 16 and the first and second bi-lumen tubes 18, 20. More particularly, the Y-connector 14 effectively divides the gas delivery lumen 24 of the quad-lumen tube 16 into the gas delivery lumen 54 of the first bi-lumen tube 18 and the gas delivery lumen of the second bi-lumen tube 20.

Figure 4:
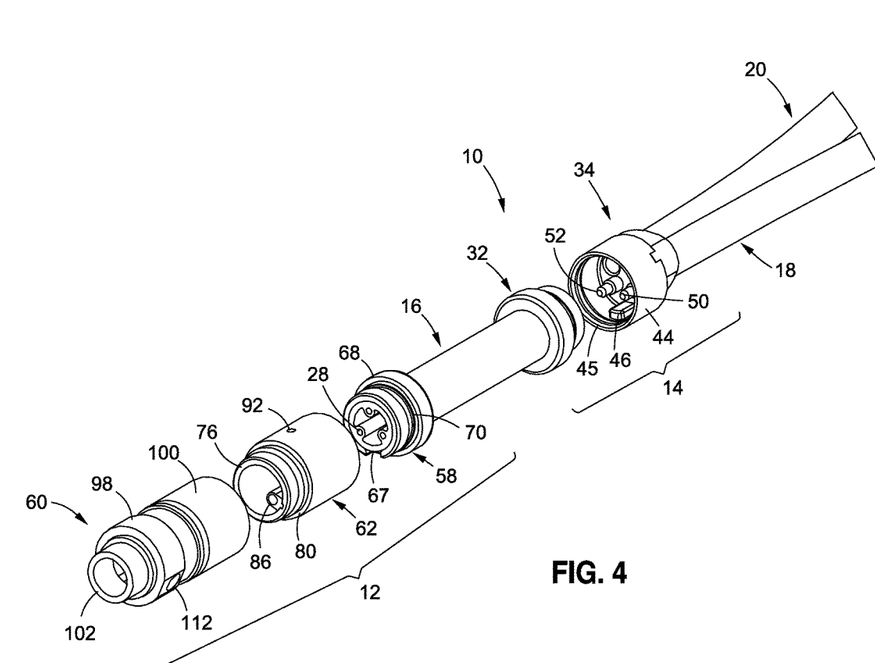
FIG. 4 is an exploded view of the delivery adaptor, tri-lumen tube, Y-connector and bi-lumen tubes shown in FIGS. 2 and 3 taken from a front perspective.
Figure 5:
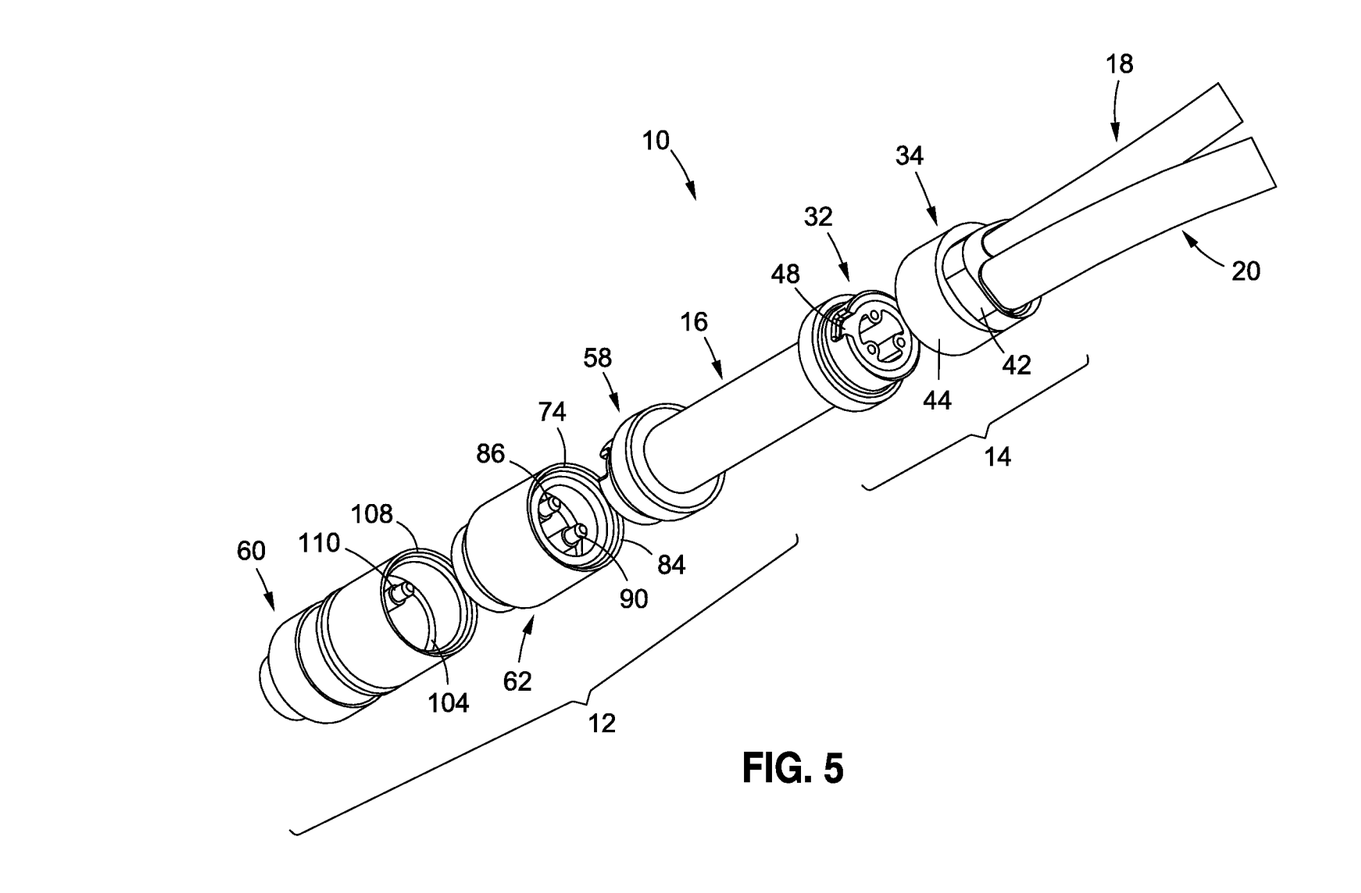
FIG. 5 is an exploded view of the delivery adaptor, tri-lumen tube, Y-connector and bi-lumen tubes shown in FIGS. 2 and 3 taken from a rear perspective.

In FIGS. 4 and 5, the male and female members 32, 34 of the Y-connector 14 are shown in a separated or disconnected state. Conversely, in FIGS. 2 and 3, the male and female members 32, 34 are depicted as being operatively connected to each other. The connection of the male and female members 32, 34 to each other is facilitated by initially advancing the reduced diameter second portion 38 of the male member 32 into the complimentary cavity 43 defined by the female member 34. In this regard, the inner diameter of the sleeve portion 44 of the female member 34 slightly exceeds the outer diameter of the second portion 38 of the male member 32, thus allowing for the slidable advancement of the second portion 38 into the cavity 43. As will be recognized, in order for the second portion 38 to be advanced into the cavity 43, the slot 48 of the male member 32 must be aligned with the tab 46 of the female member 34. In this regard, the advancement of the second portion 38 of the male member 32 into the cavity 43 of the female member 34 results in the concurrent advancement of the alignment tab 46 into the complimentary alignment slot 48. The advancement of the second portion 38 into the cavity 43 is limited by the abutment of the distal end or rim defined by the sleeve portion 44 of the female member 34 against the annular shoulder 39 defined by the male member 32. When such an abutment occurs, the O-ring 40 of the male member 32 is concurrently received into and effectively seated within the complimentary channel 45 formed within the inner surface of the sleeve portion 44 of the female member 34. The seating of the O-ring 40 into the complimentary channel 45 facilitates the formation of a fluid-tight seal between the male and female members 32, 34 of the Y-connector 14 when releasably connected to each other.

Importantly, the registry or alignment between the male and female members 32, 34 achieved by the advancement of the alignment tab 46 into the alignment slot 48 in turn facilitates the coaxial alignment of the pressure sensing port 50 of the female member 34 with the pressure sensing lumen 26 of the quad-lumen tube 16, as well as the coaxial alignment of the pilot port 52 of the female member 34 with the pilot lumen 28 of the quad-lumen tube 16. In this regard, the advancement of the second portion 38 into the cavity 43, in addition to resulting in the advancement of the tab 46 into the slot 48, also results in the concurrent advancement of the pressure sensing port 50 into the pressure sensing lumen 26, and the pilot port 52 into the pilot lumen 28. Both the pressure sensing and pilot ports 50, 52 are provided with reduced diameter distal end portions which facilitate the advancement thereof into and frictional retention within the pressure sensing and pilot lumens 26, 28, respectively. In this regard, when the second portion 38 of the male member 32 is fully received into the cavity 43 of the female member 34 in the aforementioned manner, the corresponding end of the quad-lumen tube 16 rests against the shoulders defined by the pressure sensing and pilot ports 50, 52 as a result of the formation of the distal end portions thereof with the reduced diameters as indicated above.

With the male and female members 32, 34 of the Y-connector 14 being releasably attached to each other in the aforementioned manner, the pressure sensing lumen defined by the pressure sensing port 50 is placed into fluid communication with the pressure sensing lumen 26 of the quad-lumen tube 16. As a result, the pressure sensing lumen 26 of the quad-lumen tube 16 is fluidly connected to the pressure sensing lumen 56 of the first bi-lumen tube 18 by the pressure sensing lumen defined by the pressure sensing port 50. At the same time, the pilot lumen defined pilot port 52 is placed into fluid communication with the pilot lumen 28 of the quad-lumen tube 16, thus resulting in the pilot lumen 28 being fluidly connected to the pilot lumen of the second bi-lumen tube 20 by the pilot lumen defined by the pilot port 52. As is apparent from FIG. 3, the gas delivery lumen 24 of the quad-lumen tube 16 fluidly communicates with a portion of the cavity 43, as do the first and second gas delivery lumens defined by the first and second gas delivery ports, respectively, of the female member 34. As a result, with the male and female members 32, 34 of the Y-connector 14 being releasably connected to each other in the aforementioned manner, the gas delivery lumen 24 of the quad-lumen tube 16 is effectively bifurcated or divided, and thus placed into fluid communication with the gas delivery lumen 54 of the first bi-lumen tube 18 and the gas delivery lumen of the second bi-lumen tube 20 via a portion of the cavity 43 and the first and second gas delivery lumens of the female member 34. Like the gas delivery lumen 24, the auxiliary lumen 30 of the quad-lumen tube 16 also fluidly communicates with a portion of the cavity 43 when the male and female members 32, 34 of the Y-connector 14 are releasably attached to each other. In the tubing arrangement 10, the fluid connection between the first and second bi-lumen tunes 18, 20 and the female member 34 of the Y-connector 14 as described above is unaffected by the detachment of the male and female members 32, 34 from each other. Also unaffected is the attachment between the male member 32 and the quad-lumen tube 16.

In the tubing arrangement 10, the delivery adapter 12 is adapted to allow for the selective disconnection or decoupling of the quad-lumen tube 16 from the outlet connector of the ventilator 2 of the ventilation system including the tubing arrangement 10. The delivery adapter 12 preferably has a three-piece construction, and comprises a first (male) member 58, a second (female) member 60, and a third member 62 includes both male and female structural features of the first and second members 58, 60. The first, second and third members 58, 60, 62 each have a generally tubular or annular, sleeve-like configuration, with the third member 62 being connected to and extending between the first and second members 58, 60 when the delivery adaptor 12 is in its fully assembled state.

In the delivery adapter 12, the first member 58 is identically configured to the above-described male member 32 of the Y-connector 14. In this regard, the first member 58 defines a first portion 64 which is of a first outer diameter and transitions into a second portion 66 which is of a second outer diameter less than the first outer diameter. As such, the first and second portions 64, 66 are separated from each other by continuous, annular shoulder 68. Formed within the outer surface of the second portion 66 is a continuous groove or channel which is disposed in relative close proximity to the shoulder 68 and accommodates a complementary O-ring 70. The O-ring 70 protrudes slightly outwardly beyond the outer surface of the second portion 66. The first and second portions 64, 66 further collectively define an inner surface of the first member 58 which is of a prescribed inner diameter.

The first member 58 of the delivery adapter 12 is advanced over and frictionally engaged to that end portion of the quad-lumen tube 16 opposite that which is fluidly connected to the Y-connector 14 included in the exemplary tubing arrangement 10. Thus, the first member 58 of the delivery adaptor 12 and the male member 32 of the Y-connector 14 are located on respective ones of the opposed end portions of the quad-lumen tube 16. More particularly, the first member 58 is oriented such that a corresponding end of the quad-lumen tube 16 is substantially flush or continuous with the distal rim defined by the reduced diameter second portion 66 of the first member 58. Along these lines, the inner diameter of the inner surface of the first member 58 is sized to only slightly exceed the outer diameter of the quad-lumen tube 16.

The third member 62 of the delivery adapter 12 comprises a tubular base portion 72 having a first sleeve portion 74 and a second sleeve portion 76 integrally connected to and protruding from respective ones of the opposed ends of the base portion 72. As is best seen in FIG. 3, the outer diameters of the base and first sleeve portions 72, 74 are equal to each other, though the inner diameter of the first sleeve portion 74 exceeds that of the base portion 72 thus resulting in the formation of a continuous, annular shoulder 78 therebetween. Further, the inner diameters of the base and second sleeve portions 72, 76 are substantially equal to each other, though the outer diameter of the second sleeve portion 76 is less than that of the base portion 72, thus resulting in the formation of a continuous, annular shoulder 80 therebetween. Formed within the outer surface of the second sleeve portion 76 in close proximity to the shoulder 80 is a continuous groove or channel which accommodates a complementary O-ring 82. The O-ring 82 protrudes slightly outwardly beyond the outer surface of the second sleeve portion 76. Disposed within the inner wall or surface of the first sleeve portion 74 in relative close proximity to the distal rim defined thereby is a continuous groove or channel 84. The channel 84 is sized and configured to accommodate that portion of the O-ring 70 of the first member 58 which protrudes from the outer surface of the second portion 66 thereof when the first and third members 58, 62 are releasably engaged to each other in a manner which will be described in more detail below. Also formed on the inner wall or surface of the first sleeve portion 74 proximate the channel 84 is an alignment tab, the size and shape of which is complimentary to that of a slot 67 which is formed within the second portion 66 of the first member 58. In this regard, the slot 67 is sized and configured to accommodate the tab of the third member 62 when the first and third members 58, 62 are releasably engaged to each other. In the third member 62, the base, first and second sleeve portions 72, 74, 76 collectively define a gas delivery lumen 77.

Integrally formed on the inner surface of the base portion 72 of the third member 62 is a pressure sensing port 86 which resides within the gas delivery lumen 77 and defines a pressure sensing lumen 88. The pressure sensing port 86 has an elongate, generally tubular configuration with a generally circular cross-sectional profile. The pressure sensing port 86 is also of a prescribed length, and defines opposed distal end portions. More particularly, as is best seen in FIG. 3, one end portion of the pressure sensing port 86 terminates at a location which is approximately aligned with the shoulder 80, with the opposite end portion of the pressure sensing port 86 extending into the interior of the first sleeve portion 74 and terminating at a location which is approximately aligned with the channel 84 formed in the inner surface of the first sleeve portion 74. As is further apparent from FIGS. 3 and 4, the pressure sensing port 86 does not extend along the axis of the third member 62, but rather is radially offset relative thereto. However, that end portion of the pressure sensing port 86 extending to the channel or shoulder 80 is spaced from the inner surface of the base portion 72 by a gap which is of a prescribed width. Similarly, that end portion of the pressure sensing port 86 extending to the channel 84 is similarly spaced from the inner surface of the first sleeve portion 74 by a gap which is of a prescribed width.

Figure 2:
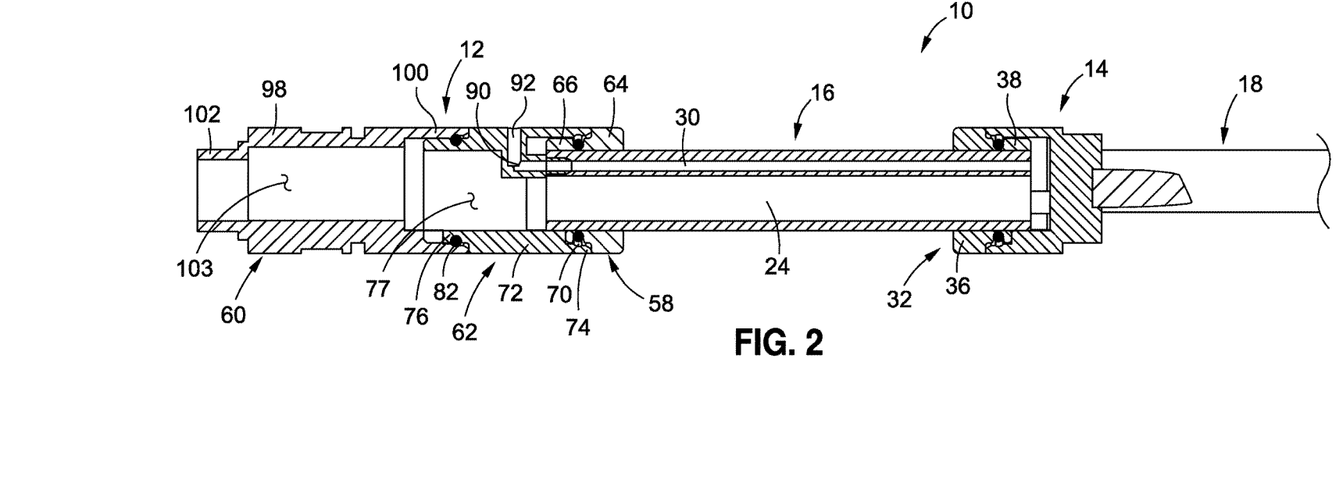
FIG. 2 is a cross-sectional view taken along line 2-2 of FIG. 1.

As best seen in FIG. 2, in addition to the pressure sensing port 86, the third member 62 further includes a fluid delivery port 90 which is also integrally connected to the inner surface of the base portion 72 and resides within the gas delivery lumen 77. As is seen in FIG. 2, similar to one of the end portions of the pressure sensing port 86, the distal end of the fluid delivery port 90 extends into the interior of the first sleeve portion 74 and terminates at a location which is approximately aligned with the channel 84 formed in the inner surface of the first sleeve portion 74. The fluid delivery port 90 defines a fluid delivery lumen 92. The fluid delivery lumen 92 extends through an approximately 90° angle, with one and of the fluid delivery lumen 92 extending to or terminating at the distal end of the fluid delivery port 90, and the opposite end of the fluid delivery lumen 92 extending to or terminating at the outer surface of the base portion 72. Like the pressure sensing port 86, the fluid delivery port 90 does not extend along the axis of the third member 62, but rather is radially offset relative thereto. However, that portion of the fluid delivery port 90 extending within the interior of the first sleeve portion 74 is separated or spaced from the inner surface thereof by a gap which is of a prescribed width. As will be described in more detail below, it is contemplated that within the confines of a ventilation system including the tubing arrangement 10 outfitted with the delivery adaptor 12, the fluid delivery lumen 92 of the fluid delivery port 90 will be used to facilitate the flow of either oxygen or water from the ventilator 2 or a source external thereto to the Y-connector 14.

The third member 62 of the delivery adaptor 12 further comprises a seal member 94 fabricated from a suitable material. The seal member 94 has an elongate, generally tubular configuration and a generally circular cross-sectional profile, thus defining a seal lumen 96. As seen in FIG. 3, the end portion of the pressure sensing port 86 extending to the shoulder 80 is advanced into the seal lumen 96. As a result, a portion of the seal member 94 extends into and thus resides within the aforementioned space or gap defined between the inner surface of the base portion 72 and the end portion of the pressure sensing port 86 which extends to the shoulder 80. The seal member 94 is sized such that the end thereof opposite the end residing with the gap terminates at approximately the distal rim defined by the second sleeve portion 76 of the third member 62. The use of the seal member 94 will be described in more detail below.

In FIGS. 4 and 5, the first and third members 58, 62 of the delivery adapter 12 are shown in the separated or disconnected state. Conversely, in FIGS. 2 and 3, the first and third members 58, 62 are depicted as being operatively connected to each other. The connection of the first and third members 58, 62 to each other is facilitated by initially advancing the reduced diameter second portion 66 of the first member 58 into the complementary interior of the first sleeve portion 74 of the third member 62. In this regard, the inner diameter of the first sleeve portion 74 of the third member 62 slightly exceeds the outer diameter of the second portion 66 of the first member 58, thus allowing for the slidable advancement of the second portion 66 into the interior of the first sleeve portion 74. In order for the second portion 66 to be advanced into the first sleeve portion 74, the slot 67 of the first member 58 must be aligned with the tab of the third member 62. The advancement of the second portion 66 of the first member 58 into the interior of the first sleeve portion 74 results in the concurrent advancement of the alignment tab into the complimentary alignment slot 67. The advancement of the second portion 66 into the interior of the first sleeve portion 74 is limited by the abutment of the distal end or rim defined by the first sleeve portion 74 of the female member 34 against the annular shoulder 68 defined by the first member 58. When such an abutment occurs, the O-ring 70 of the first member 58 is concurrently received into and effectively seated within the complimentary channel 84 formed within the inner surface of the first sleeve portion 74 of the third member 62. The seating of the O-ring 70 into the complimentary channel 84 facilitates the formation of a fluid-tight seal between the first and third members 58, 62 of the delivery adaptor 12 when releasably connected to each other.

Importantly, the registry or alignment between the first and third members 58, 62 achieved by the advancement of the alignment tab of the third member 62 into the alignment slot 67 in turn facilitates the coaxial alignment of the pressure sensing port 86 of the third member 62 with the pressure sensing lumen 26 of the quad-lumen tube 16, as well as the coaxial alignment of the fluid delivery port 90 of the third member 62 with the auxiliary lumen 30 of the quad-lumen tube 16. In this regard, the advancement of the second portion 66 into the interior of the first sleeve portion 74, in addition to resulting in the advancement of the tab into the slot 67, also results in the concurrent advancement of one of the distal end portions of the pressure sensing port 86 into the pressure sensing lumen 26, and the distal end portion of the fluid delivery port 90 into the auxiliary lumen 30. The distal end portions of the pressure sensing and fluid delivery ports 86, 90 which extend into the interior of the first sleeve portion 74 are provided with reduced diameters in comparison to the remainders thereof to facilitate their advancement into and frictional retention within the pressure sensing and auxiliary lumens 26, 30, respectively. In this regard, when the second portion 66 of the first member 58 is fully received into the first sleeve portion 74 of the third member 62 in the aforementioned manner, the corresponding end of the quad-lumen tube 16 rests against the shoulders defined by the pressure sensing and fluid delivery ports 86, 90 as a result of the formation of the distal end portions thereof with the reduced diameters.

With the first and third members 58, 62 of the delivery adaptor 12 being releasably attached to each other in the aforementioned manner, the pressure sensing lumen 88 defined by the pressure sensing port 86 is placed into fluid communication with the pressure sensing lumen 26 of the quad-lumen tube 16. At the same time, the fluid delivery lumen 92 defined by the oxygen delivery port 90 is placed into fluid communication with the auxiliary lumen 30 of the quad-lumen tube 16. As is apparent from FIG. 3, the gas delivery lumen 24 of the quad-lumen tube 16 fluidly communicates with the gas delivery lumen 77 of the third member 62, and in particular that portion thereof defined by the hollow interior of the first sleeve portion 74. The same holds true for the pilot lumen 28 of the quad-lumen tube 16.

The second member 60 of the delivery adapter 12 comprises a tubular base portion 98 having a first sleeve portion 100 and a second sleeve portion 102 integrally connected to and protruding from respective ones of the opposed ends of the base portion 98. As is best seen in FIG. 3, the maximum outer diameters of the base and first sleeve portions 98, 100 are equal to each other, though the inner diameter of the first sleeve portion 100 exceeds that of the base portion 98 thus resulting in the formation of a continuous, annular shoulder 104 therebetween. Further, the maximum outer diameter of the second sleeve portion 102 is less than that of the base portion 98, thus resulting in the formation of a continuous, annular shoulder 106 therebetween. Disposed within the inner wall or surface of the first sleeve portion 100 in relative close proximity to the distal rim defined thereby is a continuous groove or channel 108. The channel 108 is sized and configured to accommodate that portion of the O-ring 82 of the third member 62 which protrudes from the outer surface of the second sleeve portion 76 thereof when the second and third members 60, 62 are releasably engaged to each other in a manner which will be described in more detail below. Also preferably formed on the inner wall or surface of the first sleeve portion 100 proximate the channel 108 is an alignment tab, the size and shape of which is complimentary to that of a slot which is formed within the second sleeve portion 76 of the third member 62. In this regard, the slot of the third member 62 is sized and configured to accommodate the tab of the second member 60 when the second and third members 60, 62 are releasably engaged to each other. In the second member 60, the base, first and second sleeve portions 98, 100, 102 collectively define a gas delivery lumen 103.

The second member 60 further includes a pressure sensing port 110 which is integrally connected to the inner surface of the base portion 98 and resides within the gas delivery lumen 103. The pressure sensing port 110 has an elongate, generally tubular configuration with a generally circular cross-sectional profile. As is seen in FIG. 3, the distal end of the pressure sensing port 110 extends into the interior of the first sleeve portion 100 and terminates at a location which is approximately aligned with the channel 108 formed in the inner surface of the first sleeve portion 100. The pressure sensing port 100 defines a pressure sensing lumen 112. The pressure sensing lumen 112 extends through an approximately 90° angle, with one and of the pressure sensing lumen 112 extending to or terminating at the distal end of the pressure sensing port 110, and the opposite end of the pressure sensing lumen 112 extending to or terminating at the outer surface of the base portion 98. The pressure sensing port 110 does not extend along the axis of the second member 60, but rather is radially offset relative thereto. However, that portion of the pressure sensing port 110 extending within the interior of the first sleeve portion 100 is separated or spaced from the inner surface thereof by a gap which is of a prescribed width.

In FIGS. 4 and 5, the second and third members 60, 62 of the delivery adapter 12 are shown in the separated or disconnected state. Conversely, in FIGS. 2 and 3, the second and third members 60, 62 are depicted as being operatively connected to each other. The connection of the second and third members 60, 62 to each other is facilitated by initially advancing the reduced diameter second sleeve portion 76 of the third member 62 into the complementary interior of the first sleeve portion 100 of the second member 60. In this regard, the inner diameter of the first sleeve portion 100 of the second member 60 slightly exceeds the outer diameter of the second sleeve portion 76 of the third member 62, thus allowing for the slidable advancement of the second sleeve portion 76 into the interior of the first sleeve portion 100. In order for the second sleeve portion 76 to be advanced into the first sleeve portion 100, the aforementioned slot of the third member 62 must be aligned with the tab of the second member 60. The advancement of the second sleeve portion 76 of the third member 62 into the interior of the first sleeve portion 100 of the second member 60 facilitates the concurrent advancement of the alignment tab into the complimentary alignment slot. The advancement of the second sleeve portion 76 into the interior of the first sleeve portion 100 is limited by the abutment of the distal end or rim defined by the first sleeve portion 100 of the second member 60 against the annular shoulder 80 defined by the third member 62. When such an abutment occurs, the O-ring 82 of the third member 62 is concurrently received into and effectively seated within the complimentary channel 108 formed within the inner surface of the first sleeve portion 100 of the second member 60. The seating of the O-ring 82 into the complimentary channel 108 facilitates the formation of a fluid-tight seal between the second and third members 60, 62 of the delivery adaptor 12 when releasably connected to each other.

Importantly, the registry or alignment between the second and third members 60, 62 achieved by the advancement of the alignment tab of the second member 60 into the alignment slot of the third member 62 in turn facilitates the coaxial alignment of the pressure sensing port 110 of the second member 60 with the pressure sensing port 86 of the third member 62, and hence the coaxial alignment of the pressure sensing port 110 with the seal lumen 96 defined by the seal member 94. In this regard, the advancement of the second sleeve portion 76 into the interior of the first sleeve portion 100, in addition to resulting in the advancement of the tab into the slot as indicated above, also results in the concurrent advancement of the distal end portion of the pressure sensing port 110 into the seal lumen 96 of the seal member 94, as shown in FIG. 3. The distal end portion of the pressure sensing port 110 which extend into the interior of the first sleeve portion 100 is provided with a reduced diameter in comparison to the remainder thereof to facilitate its advancement into and frictional retention within the seal lumen 96.

With the second and third members 60, 62 of the delivery adaptor 12 being releasably attached to each other in the aforementioned manner, the pressure sensing lumen 112 defined by the pressure sensing port 110 is placed into fluid communication with the pressure sensing lumen 88 defined by the pressure sensing port 86 via the seal lumen 96 defined by the seal member 94. Assuming that the first and third members 58, 62 are releasably attached to each other in the aforementioned manner, the fluidly coupled pressure sensing lumens 112, 88 further fluidly communicate with the pressure sensing lumen 26 of the quad-lumen tube 16. As is apparent from FIG. 3, the gas delivery lumen 77 of the third member 62 fluidly communicates with the gas delivery lumen 103 of the second member 60, and in particular that portion thereof defined by the hollow interior of the first sleeve portion 100.

To facilitate the delivery of a prescribed mode of ventilation therapy to a patient through the use of the tubing arrangement 10, one end of each of the first and second bi-lumen tubes 18, 20 of the tubing arrangement 10 is fluidly coupled to the mask 22. The opposite end of each of the first and second bi-lumen tubes 18, 20 is fluidly connected to the female member 34 of the Y-connector 14, which is itself releasably connected to the male member 32 of the Y-connector 14 subsequent to the engagement of the male member 32 to one end of the quad-lumen tube 16. The particular manner in which both the first and second bi-lumen tubes 18, 20 and the quad-lumen tube 16 are each fluidly connected to the Y-connector 14, as well as the manner in which the male and female members 32, 34 of the Y-connector 14 are fluidly connected to each other, is set forth in detail above.

In addition, subsequent to the engagement of the first member 58 of the delivery adapter 12 to a corresponding end of the quad-lumen tube 16, the first, second and third members 58, 62, 60 of the delivery adapter 12 are releasably connected to each other, with the second member 60 of the delivery adapter 12 thereafter being fluidly coupled to the outlet connector of the ventilator 2 within the ventilation system. The particular manner in which the first, second and third members 58, 60, 62 of the delivery adaptor 12 are releasably connected to each other is also set forth in detail above. It is contemplated that the connection of the second member 60 of the delivery adaptor 12 to the outlet connector of the ventilator 2 will simultaneously accomplish two objectives. The first will be to place the pressurized gas generated by the flow generator 4 into direct fluid communication with the gas delivery lumen 103 of the second member 60 of the delivery adapter 12. The second will be to fluidly couple the pressure sensing lumen 112 of the second member 60 of the delivery adapter 12 to a corresponding pressure sensing modality which is typically included as a component of the ventilator 2 and resides within the housing thereof. However, it is contemplated that the fluid coupling of the pressure sensing lumen 112 to the pressure sensing modality may be accomplished independently of the connection of the delivery adaptor 12 to the outlet connector of the ventilator 2 which otherwise places the pressurized gas generated by the flow generator 4 into direct fluid communication with the gas delivery lumen 103 of the second member 60 as indicated above.

As indicated above, in the ventilation system including the tubing arrangement 10 outfitted with the delivery adaptor 12, the fluid delivery lumen 92 of the fluid delivery port 90 may be used to facilitate the flow of either oxygen or water from the ventilator 2 or a source external thereto to the Y-connector 14. As will be described in more detail below, if the fluid delivery lumen 92 of the third member 62 of the delivery adapter 12 is to be used for oxygen delivery (the ventilation system being operated in an "oxygen delivery mode"), such fluid delivery lumen 92 will be fluidly coupled to an independent oxygen source which may be integrated into the ventilator 2 or separate therefrom. If, on the other hand, the fluid delivery lumen 92 of the third member 62 of the delivery adapter 12 is to be used for humidification delivery (the ventilation system being operated in a "humidification delivery mode"), it is contemplated that such fluid delivery lumen 92 will be fluidly coupled to the aforementioned humidifier 6 which may be optionally integrated into the ventilator 2, or may alternatively comprise a stand-alone component separate from the ventilator 2. Along these lines, it is further contemplated that the ventilator 2 will optimally be outfitted with the humidifier 6, with the ventilation system being selectively usable in either of the oxygen or humidification delivery modes, depending on whether the fluid delivery lumen 92 of the delivery adaptor 12 is fluidly coupled to either the external oxygen source of the humidifier 6.

With the completion of the various connections described above, the activation of the flow generator 4 of the ventilator 2 within the ventilation system facilitates the flow of a pressurized fluid (e.g., air) into the gas delivery lumen 103 of the second member 60 of the delivery adapter 12, and thereafter into the gas delivery lumen 77 of the third member 62 thereof. From the gas delivery lumen 77, the pressurized air simultaneously flows into both the gas delivery lumen 24 and the pilot lumen 28 of the quad-lumen tube 16. Such flow occurs as a result of both the gas delivery and pilot lumens 24, 28 fluidly communicating with that portion of the gas delivery lumen 77 defined by the first sleeve portion 74 of the third member 62 of the delivery adapter 12. The pressurized air flowing through the gas delivery lumen 24 is introduced into the cavity 43 of the female member 34 of the Y-connector 14, and is thereafter bifurcated in the above described manner into both the gas delivery lumen 54 of the first bi-lumen tube 18 and the gas delivery lumen of the second bi-lumen tube 20. The pressurized air introduced into the pilot lumen 28 of the quad-lumen tube 16 bypasses the cavity 43, and is thereafter introduced directly into the pilot lumen of the second bi-lumen tube 20 via the pilot lumen defined by the pilot port 52 of the Y-connector 14. As such, the pilot pressure reaching the mask 22 will be proportional to the outlet pressure of the flow generator minus the pressure drop along the combined lengths of the pilot lumen 28 of the quad-lumen tube 16 and the pilot lumen of the second bi-lumen tube 20.

In addition, an uninterrupted, fluidly isolated pressure sensing flow path or line is defined between the aforementioned pressure sensing modality and the mask 22. As seen in FIG. 3, such pressure sensing flow path is collectively defined by, in sequence, the pressure sensing lumen 112 of the second member 60 of the delivery adapter 12, the seal lumen 96 of the seal member 94, the pressure sensing lumen 88 of the third member 62 of the delivery adapter 12, the pressure sensing lumen 26 of the quad-lumen tube 16, the pressure sensing lumen defined by the pressure sensing port 50 of the female member 34 of the Y-connector 14, and the pressure sensing lumen 56 of the first bi-lumen tube 18. Despite the pressure sensing ports 110, 86 not being directly connected to each other, fluid isolation is effectively maintained by the seal member 94 which confines any fluid flow between the pressure sensing lumens 112, 88 to the seal lumen 96. It is contemplated that the control of the flow generator 4, and hence the control of therapeutic pressure delivered to a patient wearing the mask 22, may be governed by the data gathered from dual pressure sensors which take measurements at the mask 22 and the output of the flow generator 4. As will be recognized, pressure sensing at the mask 22 is facilitated by the sensing line collectively defined by the aforementioned pressure sensing lumens, such sensing line extending between the mask 22 and the pressure sensing modality located remotely therefrom. A more detailed discussion regarding the use of the dual pressure sensors to govern the delivery of therapeutic pressure to the patient is found in Applicant's co-pending U.S. application Ser. No. 13/411,257 entitled Dual Pressure Sensor Continuous Positive Airway Pressure (CPAP) Therapy filed Mar. 2, 2012, the entire disclosure of which is also incorporated herein by reference.

Assuming the ventilation system is being operated in the aforementioned oxygen delivery mode, oxygen introduced into the fluid delivery lumen 92 of the delivery adapter 12 by the aforementioned oxygen delivery source, though bypassing the gas delivery lumen 77 of the third member 62, is introduced into the cavity 43 of the female member 34 of the Y-connector 14 via the auxiliary lumen 30 of the quad-lumen tube 16. As indicated above, also introduced into such cavity 43 is the pressurized air exiting the outlet end of the gas delivery lumen 24 of the quad-lumen tube 16. As such, oxygen is bled into the air stream at the outlet of the auxiliary lumen 30 of the quad-lumen tube 16 which is at Y-connector 14. Oxygen is thus bled away from the flow generator 4, but before the mask 22, in an in a high turbulence area (i.e., the cavity 43) that allows for superior mixing between the oxygen and the pressurized air flowing into the cavity 43 from the outlet end of the gas delivery lumen 24 of the quad-lumen tube 16. As a result, the chances of having oxygen flow back into the flow generator 4 are remote, even during a flow generator fault, since the path of least resistance is through the mask 22. The air and oxygen mixture created in the cavity 43 is effectively bifurcated into both the gas delivery lumen 54 of the first bi-lumen tube 18 and the gas delivery lumen of the second bi-lumen tube 20.

Assuming the ventilation system is being operated in the aforementioned humidification delivery mode, water introduced into the fluid delivery lumen 92 of the delivery adapter 12 by the aforementioned humidifier 6, though bypassing the gas delivery lumen 77 of the third member 62, is introduced into the cavity 43 of the female member 34 of the Y-connector 14 via the auxiliary lumen 30 of the quad-lumen tube 16. Also, introduced into such cavity 43 is the pressurized air (or other breathable gas) exiting the outlet end of the gas delivery lumen 24 of the quad lumen tube 16. As such, water is bled into the airstream at the outlet of the auxiliary lumen 30 of the quad-lumen tube 16 which is at the Y-connector 14. Humidity is thus delivered away from the flow generator 4, but before the mask 22, in an in a high turbulence area (i.e., the cavity 43) that allows for superior mixing between the humidity and the pressurized air flowing into the cavity 43 from the outlet end of the gas delivery lumen 24 of the quad-lumen tube 16. As a result, the chances of having water spilling back into the flow generator 4 are remote, even during a flow generator fault. This solves a common problem that traditional humidifiers have, where water is split in the ventilator damaging the interior components thereof (e.g., the blower, sound absorbing foam, sensors, etc.). The air and water mixture created in the cavity 43 is effectively bifurcated into both the gas delivery lumen 54 of the first bi-lumen tube 18 and the gas delivery lumen of the second bi-lumen tube 20.

In order to ensure that the water is properly mixed with the airstream or other breathable gas at the Y-connector 14, it is contemplated that the outlet end of the auxiliary lumen 30 of the quad-lumen tube 16 which is at the Y-connector 14 may be outfitted with a humidity delivery system 114 which is shown in phantom in FIG. 8. It is contemplated that such humidity delivery system 114 may be a selectively permeable membrane (e.g., Gore-Tex®) that delivers gaseous water, a valve that delivers small droplets of water, or a nebulizer that delivers pulverized water. In each of these potential variants, the water is delivered, in different forms, in the highly turbulent area of the cavity 43 of the Y-connector 14 in order to facilitate mixing with the airstream or other breathable gas.

Since the outlet end of the auxiliary lumen 30 of the quad-lumen tube 16 is preferably outfitted with one of the aforementioned humidity delivery systems 114, it is contemplated that the tubing arrangement 10, and in particular the male member 32 of the Y-connector 14 and the first member 58 of the delivery adapter 12, may be configured in a manner which ensures that the male member 32 may not be inadvertently connected to the third member 62 of the delivery adapter 12 despite the male member 32 and the first member 58 having structural features which are substantially similar to each other. In this regard, it is important that the humidity delivery system 114 outfitted onto the outlet end of the auxiliary lumen 30 be disposed at the cavity 43 of the Y-connector 14, and not at the delivery adapter 12 as could otherwise result in no humidification reaching the mask 22 or other patient interface. To accomplish this objective, in the tubing arrangement 10, the inadvertent reversal of the quad-lumen tube 16 from its proper orientation may be prevented by forming the slot 48 of the male member 32 to be of a size and/or shape which differ from that of the slot 67 included in the first member 58. In this regard, the slot 48 may be sized to accept only the tab 46 of the female member 34 of the Y-connector 14 which has a complementary configuration, and not the tab preferably formed on the third member 62 of the delivery adapter 12 and having a configuration which is complementary to that of the slot 67.

As seen in FIGS. 6 and 7, it is contemplated that the humidifier 6 of the ventilator 2 may be provided in either of two (2) exemplary configurations. Within each such configuration, the humidifier 6 includes a reservoir or water supply 8 which is integrated therein and is fluidly coupled to the fluid delivery lumen 92 of the delivery adapter 12. The water in the water supply 8 can be at room temperature or heated to a preset temperature.

However, in order to drive the water delivery from the water supply 8 through the fluid delivery lumen 92 and the auxiliary lumen 30 into the cavity 43, a pressure source is also required, such pressure source interacting with the water supply 8 and/or the fluid delivery lumen 92. In the configuration shown in FIG. 6, the blower or flow generator 4 of the ventilator 2 is used as the pressure source. In this implementation, a pressure tap from the flow generator 4 to the water supply 8 or fluid delivery lumen 92 is needed, with the pressure swinging up and down in accordance with the patient's breaths. This will allow a breath by breath humidity delivery, particularly if a valve or a nebulizer is used at the Y-connector 14 as the humidity delivery system 114. Stated another way, with the flow generator 4 being used as the pressure source, the water delivery pressure is synchronized with the patient's breath rate since the flow generator 4 increases the delivered pressure when the patient inhales. As such, the pressure in the water line collectively defined by the fluid delivery lumen 92 and the auxiliary lumen 30 works basically as a valve. Along these lines, the increase in pressure can thus be used to operate the humidity/water delivery system (e.g., the delivery valve is opened or the water is nebulized above a certain pressure threshold).

In the alternative, as seen in FIG. 7, the pressure source may be a pressurization device 9 which is included in the humidifier 6 and is operatively coupled to the water supply 8 and/or the fluid delivery lumen 92. It is contemplated that the pressurization device 9, if integrated into the humidifier 6 and used as the pressure source, may be electrically connected to the flow generator 4 and supplied with AC or DC therefrom. As a further potential alternative, use of the flow generator 4 or pressurization device 9 as the pressure source may be eliminated in favor of employing a wicking material in the auxiliary lumen 30 which provides a capillary action to facilitate flow to the cavity 43 of the Y-connector 14.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A fluid conduit for fluidly for coupling a flow generator to a ventilation mask in a respiratory assistance system, the fluid conduit comprising:
   a delivery adaptor defining a gas delivery lumen which is fluidly connectible to the flow generator for receiving a pressurized fluid from the flow generator, a fluid delivery lumen which is fluidly isolated from the gas delivery lumen within the delivery adaptor and fluidly connectible to an independent oxygen or water source separate from the pressurized fluid emanating from the flow generator, and a pressure sensing lumen which is fluidly isolated from the gas delivery and fluid delivery lumens and is fluidly connectible to a pressure sensing modality;
   a connector defining a gas delivery lumen and a pressure sensing lumen that are fluidly isolated from each other; and
   at least a main delivery tube which fluidly couples the delivery adaptor to the mask via the connector, the main delivery tube defining a gas delivery lumen, a fluid delivery lumen, and a pressure sensing lumen that are fluidly isolated from each other, the main delivery tube configured to connect to the delivery adaptor and the connector such that i) the gas delivery lumen of the delivery adaptor is fluidly connected to the gas delivery lumen of the connector via the gas delivery lumen of the main delivery tube, ii) the pressure sensing lumen of the adapter is fluidly connected to the pressure sensing lumen of the connector via the pressure sensing lumen of the main delivery tube, and iii) the fluid delivery lumen of the delivery adaptor is fluidly connected to the gas delivery lumen of the connector via the fluid delivery lumen of the main delivery tube so as to facilitate the flow of oxygen or water into a pressurized fluid flowing in the gas delivery lumen of the connector from the main delivery tube toward the mask.

2. The fluid conduit of claim 1 wherein the delivery adaptor comprises:
a first member coupled to the main delivery tube;
a third member releasably attached to the first member, the third member including a gas delivery lumen which is fluidly coupled to the main delivery tube, a pressure sensing port defining a pressure sensing lumen which is fluidly coupled to the main delivery tube, and a fluid delivery port defining a fluid delivery lumen which is fluidly coupled to the main delivery tube; and
a second member releasably attached to the third member, the second member including a gas delivery lumen which is fluidly coupled to the gas delivery lumen of the third member, and a pressure sensing port defining a pressure sensing lumen which is fluidly coupled to the pressure sensing lumen of the third member.

3. The fluid conduit of claim 2 wherein the delivery adaptor further comprises a seal member which is cooperatively engaged to at least portions of the pressure sensing ports of each of the second and third members, the seal member defining a seal lumen which facilitates fluid communication between the pressure sensing lumens defined by the pressure sensing ports of each of the second and third members.

4. The fluid conduit of claim 2 wherein the third member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion thereof;
the pressure sensing and fluid delivery ports of the third member each being integrally connected to the inner surface of the base portion thereof and protruding into the interior of at least the first sleeve portion thereof, with one end of the fluid delivery lumen of the third member extending to the outer surface of the base portion thereof.

5. The fluid conduit of claim 4 wherein the second member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion;
the pressure sensing port of the second member being integrally connected to the inner surface of the base portion and protruding into the interior of at least the first sleeve portion thereof, with one end of the pressure sensing lumen of the second member extending to the outer surface of the base portion thereof.

6. The fluid conduit of claim 1 wherein the fluid conduit further comprises:
a first bi-lumen tube which is fluidly coupled to the main delivery tube via the connector and is fluidly connectible to the ventilation mask; and
a second bi-lumen tube which is fluidly coupled to the main delivery tube via the connector and is fluidly connectible to the ventilation mask.

7. The fluid conduit of claim 6 wherein:
the main delivery tube further defines a valve pilot lumen which is fluidly isolated from the gas delivery, fluid delivery, and pressure sensing lumens of the main delivery tube and fluidly coupled to the gas delivery lumen of the delivery adaptor when the main delivery tube is connected to the delivery adaptor;
the connector further defines a valve pilot lumen that is fluidly isolated from the gas delivery and pressure sensing lumens of the connector and fluidly coupled to the valve pilot lumen of the main delivery tube when the main delivery tube is connected to the connector;
the first bi-lumen tube defines a gas delivery lumen which is fluidly coupled to the gas delivery and fluid delivery lumens of the main delivery tube via the gas delivery lumen of the connector, and a pressure sensing lumen which is fluidly isolated from the gas delivery lumen thereof, and is fluidly coupled to the pressure sensing lumen of the main delivery tube via the pressure sensing lumen of the connector; and
the second bi-lumen tube defines a gas delivery lumen which is fluidly coupled to the gas delivery and fluid delivery lumens of the main delivery tube via the gas delivery lumen of the connector, and a valve pilot lumen which is fluidly coupled to the valve pilot lumen of the main delivery tube via the valve pilot lumen of the connector.

8. The fluid conduit of claim 7 wherein the connector includes at least first and second members which are releasably connectable to each other as allows for the selective detachment and separation of the main delivery tube from each of the first and second bi-lumen tubes.

9. The fluid conduit of claim 8 further comprising a humidity delivery system operatively integrated into the fluid delivery lumen of the main delivery tube at the connector.

10. The fluid conduit of claim 7 wherein the delivery adaptor comprises:
a first member coupled to the main delivery tube;
a third member releasably attached to the first member, the third member including a gas delivery lumen which is fluidly coupled to the gas delivery lumen of the main delivery tube, a pressure sensing port defining a pressure sensing lumen which is fluidly coupled to the pressure sensing lumen of the main delivery tube, and a fluid delivery port defining a fluid delivery lumen which is fluidly coupled to the fluid delivery lumen of the main delivery tube; and
a second member releasably attached to the third member, the second member including a gas delivery lumen which is fluidly coupled to the gas delivery lumen of the third member, and a pressure sensing port defining a pressure sensing lumen which is fluidly coupled to the pressure sensing lumen of the third member.

11. The fluid conduit of claim 10 wherein the delivery adaptor further comprises a seal member which is cooperatively engaged to at least portions of the pressure sensing ports of each of the second and third members, the seal member defining a seal lumen which facilitates fluid communication between the pressure sensing lumens defined by the pressure sensing ports of each of the second and third members.

12. The fluid conduit of claim 10 wherein the third member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion thereof;

the pressure sensing and fluid delivery ports of the third member each being integrally connected to the inner surface of the base portion thereof and protruding into the interior of at least the first sleeve portion thereof, with one end of the fluid delivery lumen of the third member extending to the outer surface of the base portion thereof.

13. The fluid conduit of claim 12 wherein the second member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion;
the pressure sensing port of the second member being integrally connected to the inner surface of the base portion and protruding into the interior of at least the first sleeve portion thereof, with one end of the pressure sensing lumen of the second member extending to the outer surface of the base portion thereof.

14. The fluid conduit of claim 1 further comprising:
at least one ancillary delivery tube which is fluidly coupled to the main delivery tube via the connector and is fluidly connectible to the ventilation mask.

15. The fluid conduit of claim 14 wherein the ancillary delivery tube defines at least a gas delivery lumen which is fluidly coupled to the gas delivery and fluid delivery lumens of the main delivery tube via the gas delivery lumen of the connector, and a pressure sensing lumen which is fluidly isolated from the gas delivery lumen thereof, and is fluidly coupled to the pressure sensing lumen of the main delivery tube via the pressure sensing lumen of the connector.

16. The fluid conduit of claim 15 wherein the delivery adaptor comprises:
a first member coupled to the main delivery tube;
a third member releasably attached to the first member, the third member including a gas delivery lumen which is fluidly coupled to the gas delivery lumen of the main delivery tube, a pressure sensing port defining a pressure sensing lumen which is fluidly coupled to the pressure sensing lumen of the main delivery tube, and a fluid delivery port defining a fluid delivery lumen which is fluidly coupled to the fluid delivery lumen of the main delivery tube; and
a second member releasably attached to the third member, the second member including a gas delivery lumen which is fluidly coupled to the gas delivery lumen of the third member, and a pressure sensing port defining a pressure sensing lumen which is fluidly coupled to the pressure sensing lumen of the third member.

17. The fluid conduit of claim 16 wherein the delivery adaptor further comprises a seal member which is cooperatively engaged to at least portions of the pressure sensing ports of each of the second and third members, the seal member defining a seal lumen which facilitates fluid communication between the pressure sensing lumens defined by the pressure sensing ports of each of the second and third members.

18. The fluid conduit of claim 16 wherein the third member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion thereof;
the pressure sensing and fluid delivery ports of the third member each being integrally connected to the inner surface of the base portion thereof and protruding into the interior of at least the first sleeve portion thereof, with one end of the fluid delivery lumen of the third member extending to the outer surface of the base portion thereof.

19. The fluid conduit of claim 18 wherein the second member of the delivery adaptor comprises:
a base portion having opposed ends, an inner surface partially defining the gas delivery lumen thereof, and an outer surface; and
first and second sleeve portions integrally connected and protruding from respective ones of the opposed ends of the base portion;
the pressure sensing port of the second member being integrally connected to the inner surface of the base portion and protruding into the interior of at least the first sleeve portion thereof, with one end of the pressure sensing lumen of the second member extending to the outer surface of the base portion thereof.

* * * * *